US006274304B1

(12) United States Patent
Buschek et al.

(10) Patent No.: US 6,274,304 B1

(45) Date of Patent: Aug. 14, 2001

(54) APPARATUS WITH DESICCANT CHAMBER AND METHOD OF USING

(75) Inventors: Herbert Buschek, Weilheim; Michael Kuehnl, München; Roland Ihrig, Lampertheim; Klaus Erler, Weilheim; Maria Cully, Krailling, all of (DE)

(73) Assignee: Roche Diagnostics GmbH, Mannhein (DE)

( * ) Notice: Subject to any disclaimer, the term of this patent is extended or adjusted under 35 U.S.C. 154(b) by 0 days.

(21) Appl. No.: 08/195,018

(22) Filed: Feb. 14, 1994

(30) Foreign Application Priority Data

Feb. 13, 1993 (DE) ............................................ 43 04 450

(51) Int. Cl.[7] ..................................................... C12Q 1/00

(52) U.S. Cl. ............................................... 435/4; 215/227

(58) Field of Search .................................. 435/4; 55/275, 55/316, 387, 388, 389; 215/227, 228, 308, 316

(56) References Cited

U.S. PATENT DOCUMENTS 1,655,248 * 1/1928 Sharp .................................. 215/316
2,317,882 * 4/1943 Boesel ................................. 215/316
2,446,361 * 8/1948 Clibbon ............................... 215/316
2,487,620 * 11/1949 Waller ................................ 215/316
2,548,168 * 4/1951 Luce ................................... 215/316
2,676,078 * 4/1954 Young ................................. 215/316
3,732,627 * 5/1973 Wertheim .................................. 34/9
3,990,872 * 11/1976 Cullen .................................. 55/274
4,119,407 10/1978 Goldstein et al. ..................... 422/58
4,350,508 * 9/1982 Santoro ................................. 55/275
4,545,492 * 10/1985 Firestone ............................. 215/227
4,834,234 * 5/1989 Sacherer .............................. 206/204
5,128,104 7/1992 Murphy et al. ...................... 422/102

* cited by examiner

*Primary Examiner*—Ralph Gitomer
(74) *Attorney, Agent, or Firm*—Arent Fox Kintner Plotkin & Kahn, PLLC

(57) ABSTRACT

There is provided a system for the preparation of liquids from at least one solid and at least one liquid phase. The system is composed of a vessel in which the solid or solids are located and a drying chamber which is connected to the vessel or can be connected to the vessel. The drying chamber is separated from the vessel interior by a separating means which is permeable to water vapour but is impermeable to liquids. The system is suitable for the production of liquids from moisture-sensitive solids. These solids can be stored in the vessel since the air humidity in the interior is lowered by the desiccant. The preparation of the liquid by addition of a liquid phase can be carried out in one and the same vessel since the desiccant is separated from the vessel interior.

23 Claims, 4 Drawing Sheets

APPARATUS WITH DESICCANT CHAMBER AND METHOD OF USING

The invention concerns a system for the preparation of liquids from at least one solid and at least one liquid phase, the system consisting of a storage vessel with the solid and a drying chamber with a desiccant. In addition the invention concerns a process for the production of a solution, suspension or emulsion using the system according to the invention. The process comprises the steps of storing a solid in the system, adding a liquid phase to the solid and mixing in order to produce a solution, suspension or emulsion. In a preferred application the system serves to produce reagent solutions.

A problem which frequently occurs in laboratories is that of preparing solutions from liquids and moisture-sensitive solids. The stability of many solids is limited in the presence of water vapour since they decompose. The occurrence of such problems ranges from everyday examples such as e.g. the preparation of foods from dry powder, over the preparation of solutions in the chemical laboratory, to clinical analytical solutions. Especially in the latter case it is necessary to prepare a solution from a solid and a liquid component shortly before use if the final analytical solution has only a limited stability.

The prevailing problem is often solved by either predrying the moisture-sensitive solid and packaging it in a water-vapour-tight package or it is packaged together with hygroscopic substances in order to dry it and maintain dryness. In order to prepare the solution, a certain amount of the substance is weighed and dissolved in a measured amount of liquid. The process is imperfect, in particular for analytical solutions, since the quantitative transfer of the solid into a vessel, the addition of an exactly defined amount of solvent and a complete dissolution is difficult. The said process not only requires trained personnel but also elaborate laboratory equipment.

In the case of so-called test kits the user undertakes the preparation of the liquid by preparing the analytical solution from the portioned, i.e. already weighed solids by addition of liquid according to the instructions of the manufacturer of the kit. Stirrers or mixers can relieve the user of the task of dissolving the solids. However, in these cases it is nevertheless necessary to transfer a solid into a vessel for dissolution. Consequently a defined amount of solid in the form of tablets, powders or granulates has to be introduced into a vessel in order to prepare a solution of a defined concentration. In a known reagent stocking system (DE-40 39 580) the reagent is transferred from a special container into a mixing vessel by the opening of a chamber in which the reagent is located when it is screwed onto the vessel. In order to prepare a solution of an exactly defined concentration it is necessary to rinse the chamber. This necessitates laboratory personnel or an elaborate rinsing device.

The object of the invention is to simplify the preparation of liquids from moisture-sensitive solids and liquids by providing a vessel suitable for drying and maintaining dryness. In particular it is intended to facilitate the preparation of an analytical solution by untrained personnel even under conditions of poor infrastructure.

The object is achieved with the system for the preparation of a liquid from at least one solid and at least one liquid phase by the combination of a vessel which contains the at least one solid and has a volume which is sufficient to receive the at least one solid and the at least one liquid phase, a desiccant chamber which contains a desiccant (D)

and a separating element which closes the desiccant chamber in such a way that the desiccant can exchange water vapour at any time with the contents of the vessel but direct contact of liquid or solid contents of the vessel with the desiccant is essentially impossible.

Accordingly the object is achieved by the combination of the following elements:

A vessel in which at first the solid is situated and in which the dissolution of the solid takes place.

A drying chamber connected to the vessel in which a desiccant is located.

The solid of the solution to be prepared can be present in various forms. These include powder, tablets, granulates, pellets or lyophilisates manufactured by freeze-drying.

A solution of several substances can be prepared by using a solid consisting of several components. If the components are mutually incompatible in solution or in the presence of humidity i.e. they then react with each other in an undesired manner, it is, however, in many cases possible to store the substances together in a dry state without their reacting with each other. The storage stability of the solid is increased by a drying chamber which maintains the humidity in the interior of the vessel at a low level. The presence of a desiccant in a chamber which can exchange water vapour with the vessel interior leads to a decrease in the partial water vapour pressure in the vessel interior. In the case of solids which have a residual moisture content due to the manufacturing process it is additionally possible to store them in the system according to the invention in order to dry them or to remove the residual moisture.

The liquid phase can represent a liquid composed of a pure substance (e.g. distilled water) or a mixture of several liquids. The liquid phase can also for example contain buffers, stabilisers or further dissolved substances so that the stability of the prepared liquid is increased and its function is ensured.

In order to prepare the liquid, the liquid phase is added to the solid in the vessel. This can either be carried out manually or automatically by a device. In cases in which the prepared liquid does not have to have an exact concentration since a wide range of reagent concentrations lead to the same analytical results, the measuring of the liquid phase can for example be achieved by marks on the vessel wall. For example enzymes may completely convert an analyte so that the result of the determination is independent of the enzyme concentration in the reagent over wide ranges. In contrast for the preparation of a suitable standard solution for titration analyses, the addition of a defined amount of liquid phase, characterized by its volume or its weight, to a defined amount of solid is necessary. The preparation of the solution is achieved by manual or mechanical mixing of the solid and the liquid phase. It is possible to standardize the preparation of numerous analytical solutions. In these embodiments the liquid phase already contains further components, e.g. buffer and auxiliary substances, so that always one and the same liquid phase can be used for many different analytical solutions.

The liquids produced from the solid and liquid phase in the system according to the invention can be solutions, suspensions or emulsions. For example an emulsion for the detection of the enzyme lipase can be prepared by addition of water to a solid which comprises the following substances: Tris(hydroxymethyl)aminomethane (Tris), sodium deoxycholate, $CaCl_2$, triolein, colipase, $NaN_3$.

According to the invention the system contains a vessel and a drying chamber which are separated by a separating layer which prevents entry of liquid into the desiccant. Thus the separating layer fulfils two contradictory requirements. On the one hand it is permeable to water vapour and thus enables transfer of water from the vessel interior into the drying chamber via the gas phase, on the other hand it has a barrier effect for water in a condensed phase. For the preparation process this results in the simplification that the preparation of the solution can take place in the same vessel in which the moisture-sensitive solid has previously been stored. In a preferred embodiment, the solid is already dispensed into the vessel during the manufacture of the system. In this case it is not necessary for the user to transfer the solid into the vessel. This additionally eliminates the problem of the user having to weigh out and transfer substances which may be sensitive to moisture or even hygroscopic. The manufacturer can fill the system under dry room conditions and using highly accurate balances. Thus it is possible, even for users without a laboratory, to prepare standardized analytical solutions from moisture-sensitive solids.

A preferred embodiment enables a particularly simple, safe and reliable handling in which the solid is located in a vessel which is large enough to receive the solution which is formed. This vessel has a closure, e.g. a stopper or a screw cap, to which a desiccant chamber is attached in such a way that the desiccant which it contains can take up water vapour from the interior of the vessel when the vessel is closed. In this embodiment the drying chamber can serve to dry and/or maintain dryness of the solid and it can also be used as a closure when preparing liquids.

It is also possible to mount the drying chamber in the vessel and to use a separate component to close the vessel. In addition embodiments are possible in which no means of opening by for example a screw cap or a cover is provided. In these embodiments the solid and the drying chamber can already be introduced into the vessel during the manufacture of the vessel. The liquid phase can be dispensed into the vessel before the user uses the liquid e.g. by injection with a cannula.

The system according to the invention for the preparation of liquids in its various embodiments offers solutions to problems some of which have contradictory requirements.

- Conventional vessels constructed for receiving liquids can also be used to store and re-dry moisture-sensitive solids by the use according to the invention of the drying stopper. The vessel and desiccant stopper thus become a new functional unit.
- The system for preparing solutions allows the dispensing of moisture-sensitive filling materials in containers which are not completely water-vapour-tight for the purpose of putting them into circulation.
- Solid filling materials may, due to the manufacturing process, have a higher mobile moisture content when they are dispensed than is desirable for storage. Such filling materials can be redried with the system according to the invention to the minimum residual moisture content necessary for stability.
- The separating element combines a high vapour permeability with a good barrier effect against liquids.

A process for the preparation of liquids using the system according to the invention can be carried out in the following steps:

- Storage of a solid in a closed vessel.
- Opening the system e.g. by unscrewing a cap.
- Filling the vessel which already contains the solid with the liquid phase.
- Closing the system e.g. by screwing on a cap.
- Mixing the liquid phase and solid.

The filling of the vessel with the liquid phase can be carried out manually or by machine, the automatic filling of the vessel within an automated analyser representing a preferred embodiment. The vessel can be closed with the cap belonging to the system or with a further cap. In this step in the process it is also possible to employ manual as well as automatic procedures. In special embodiments of the process according to the invention it is possible to omit the step of closing the vessel when liquid does not escape from the vessel during mixing. This can for example be achieved by stirring or suitable rotation of the vessel. Apart from mechanical stirring with a rotor which is immersed in the liquid, so-called magnetic stirrers are known among others in the state of the art in which a usually rod-shaped magnet is located within the vessel that is brought into motion by a magnetic field. In addition rockers for bacterial cultures are for example known which mix the contents of a vessel without the substances in the vessel escaping through an opening present in the upper side of the vessel. If the mixing process is carried out in a closed vessel then the aforementioned methods are available. In addition it is possible to use those methods in which the vessel can take up any position such as is usually the case for manual mixing. After the mixing process the prepared liquid is present in a vessel. It can be withdrawn from this for example by piercing the vessel with a cannula or by further devices provided in the vessel. However, the liquid is preferably withdrawn after removing the cap containing the desiccant by opening the vessel.

An advantage of the system according to the invention is that the storage vessel for the solid can also serve as the vessel to mix the solid with the liquid phase and to store the prepared liquid without it being necessary to close or remove the desiccant chamber after addition of the liquid phase.

A further advantage of the system is that the cap containing the desiccant can be used during storage of the solid as well as during storage of the prepared liquid and preferably even during mixing of the solid with the liquid phase.

The invention is elucidated further in the following by the figures:

A preferred embodiment of the desiccant chamber is that as a result of its construction it is suitable for closing the vessel. Such a desiccant chamber is denoted desiccant stopper in the following.

Figure 1:
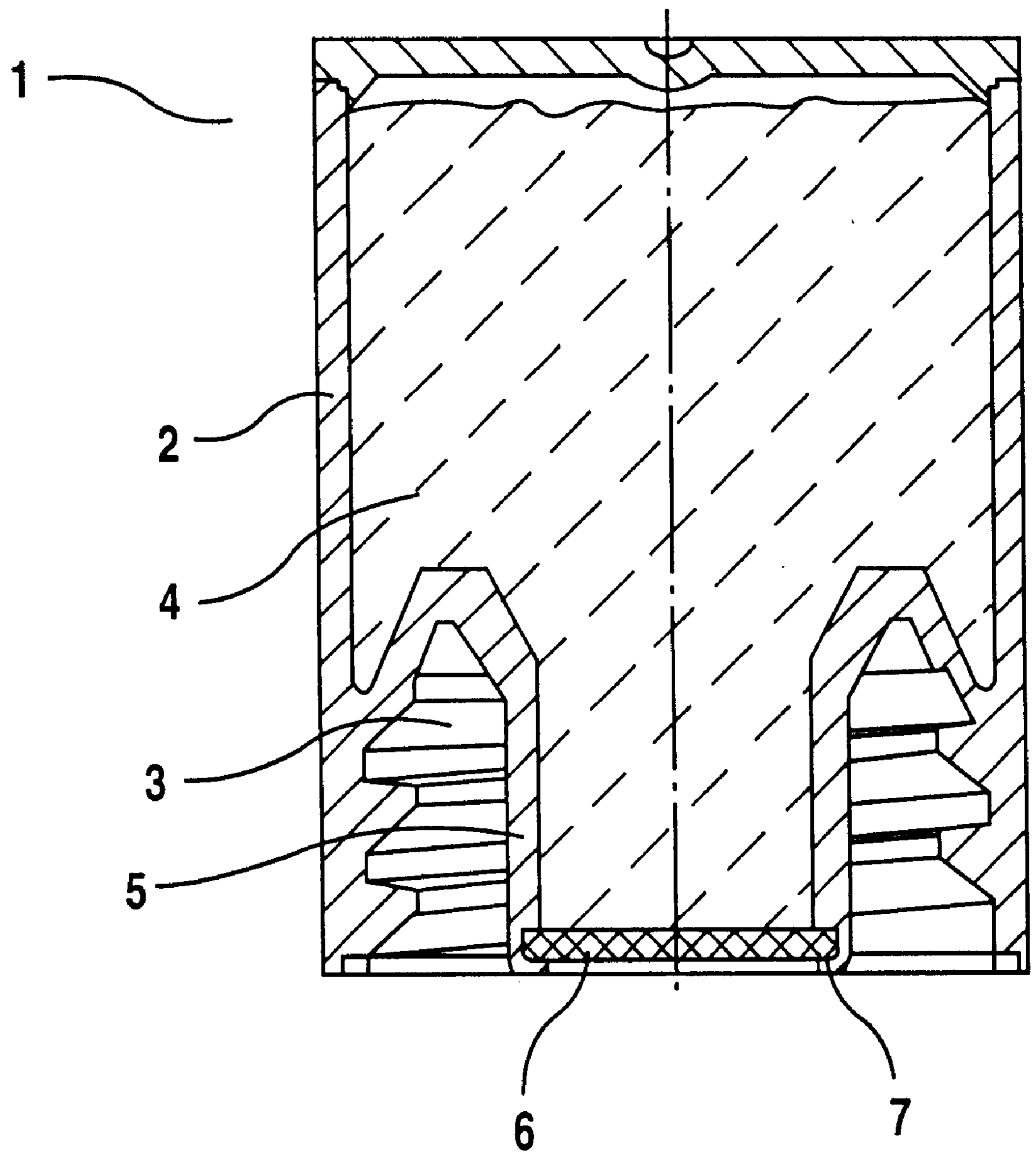
FIG. 1: A desiccant chamber with desiccant according to the invention in longitudinal section.

The desiccant stopper (1) in FIG. 1 is closed to the outside by a wall (2). This can consist of numerous materials e.g. plastic, metal and cardboard. However, in the preferred case the wall is comprised of a plastic since this material combines some advantageous properties. Plastics of adequate wall thickness, preferably larger than 0.5 mm, have the property of separating the desiccant in the interior of the stopper from the environment in such a way that although humidity can be exchanged to a slight extent between the environment and desiccant, a substantial consumption of the desiccant by external moisture is, however, avoided. In addition plastics can easily be made into shapes which include a thread (3) as well as a space for the desiccant (4).

The desiccant (4) is located in the interior of the stopper. The known substances from the specialist literature are available when selecting a suitable desiccant such as molecular sieves, silica gel, sodium sulfate, potassium sulfate etc. A zeolite type of molecular sieve which is suitable for the stated use is obtainable from the Grace GmbH Company under the name "Molekularsieb Typ 511". The amount of desiccant used and thus the drying capacity must be such that, if desired, a possible mobile moisture content of the solid is taken up and that humidity which penetrates from outside can be absorbed up to the time of preparing the solution. On the other hand the amount of desiccant should be small enough that when the prepared liquid is stored in the preparation system there is no significant change in concentration caused by uptake of water from the solution by the desiccant. In the case of the desiccant amounts which are preferably used in the range of a few grams and liquid amounts in the range of decilitres, the error caused by the desiccant is in an acceptable range for analytical solutions. In many cases the liquid will be used in an analytical apparatus soon after its preparation. In a preferred embodiment the vessel without desiccant stopper is placed at a location provided therefor within the apparatus. In this case the liquid is only in direct or indirect contact with the desiccant stopper during the period of its preparation. Thus a drying effect of the solution is likely to occur only to a very slight extent. The drying effect can in all cases be prevented by replacing the desiccant stopper after mixing solid and liquid phase with a cap without desiccant.

The separating element (6) which separates the desiccant and the interior of the vessel from one another represents an important aspect of the invention. The separating element preferably has a critical surface tension for wetting of from 25 to 65 mN\m, more preferably from 30 to 40 mN\m. The material of the separating element is of such a kind that although it is permeable to water vapour it is a complete barrier to the final reagent solutions. In recent years special plastics have been developed which combine both these properties (e.g. EP-A 0 500 173). However, it is also possible to use other materials such as e.g. impregnated fabrics and cardboard. In a preferred embodiment of the invention cardboard with a surface tension is used which prevents liquids from entering into the desiccant chamber and permeation of the desiccant with liquid. Suitable cardboards are for example sold by the Buchmann GmbH Company under the name GC1 and GC2 and by the Laakmann GmbH Company under the name UD2. The water repellent action is primarily ensured by a coating, the so-called coat, which is composed of pigments and synthetic binding agents. If the cardboard has a surface tension which is less than 70 mN/m then the cardboard can no longer be wetted by water and penetration of water is basically impossible; it is, however, still permeable to water vapour. In the case of liquids which have a smaller surface tension, a separating element with a smaller surface tension is also necessary in order to prevent penetration of liquids. The surface tension of the cardboard can be determined in a simple manner with commercial test inks from e.g. the "Arcotec Oberflachentechnik GmbH Company".

A possible arrangement for the separating element is shown in FIG. 1. The separating element (6) is fitted into a hollow plug (5) in such a way that the liquid is prevented from passing from the vessel interior to the desiccant. In a preferred embodiment this is achieved by the fact that the separating element (6) lies on the opening of the hollow plug (5) that faces the vessel interior. A flanging (7) is connected mechanically to the hollow plug which is used to mount the separating element (6) on the hollow plug. The flanging (7) closes the space formed by the desiccant chamber (4) and separating element (6) to liquids. Possible slight leakiness is sealed by the fact that the separating element swells up on contact with water and fills the gaps. Example 1 demonstrates the separating effect of the cardboard used towards an aqueous reagent liquid even on direct contact.

Figure 2:
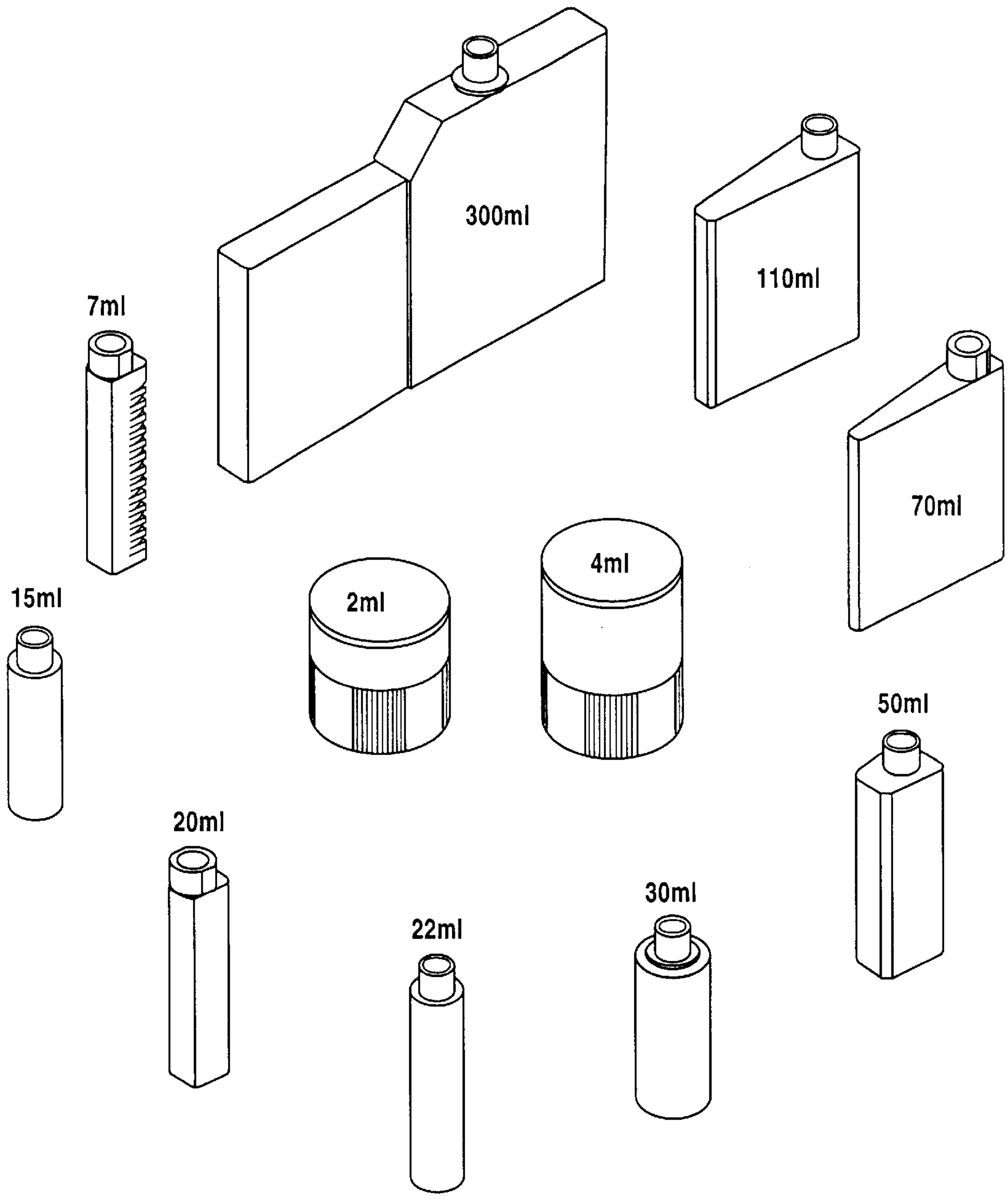
FIG. 2: Possible embodiments of the vessel (arranged in a circle) and of the desiccant chamber (in the middle).

FIG. 2 shows a circular arrangement of vessels with desiccant stoppers according to the invention and in their middle it shows two desiccant stoppers with two and four ml capacity for desiccants. Not only the shapes but also the wall thicknesses of the vessels can be varied within wide limits. The materials of the vessels must be impermeable to water, but can be partly permeable to water vapour. Plastics are for example suitable for the vessel such as those which are used in the manufacture of bottles for storing liquids. However, wall thicknesses which are larger than 0.5 mm are preferred for reasons of mechanical stability and water vapour permeability. The manufacturing methods for the vessels, e.g. injection moulding or injection blowing, are not subject to any restrictions provided an adequate wall thickness can be ensured.

Figure 3C:
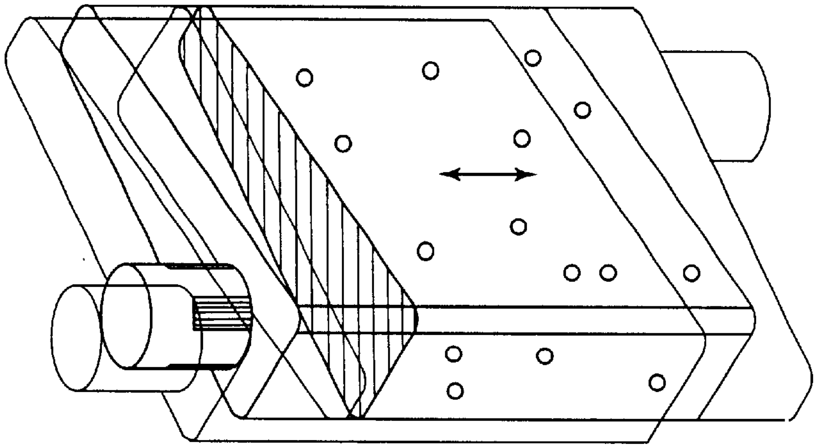
FIG. 3: Steps in the process of preparing a liquid using the system according to the invention.
Figure 3B:
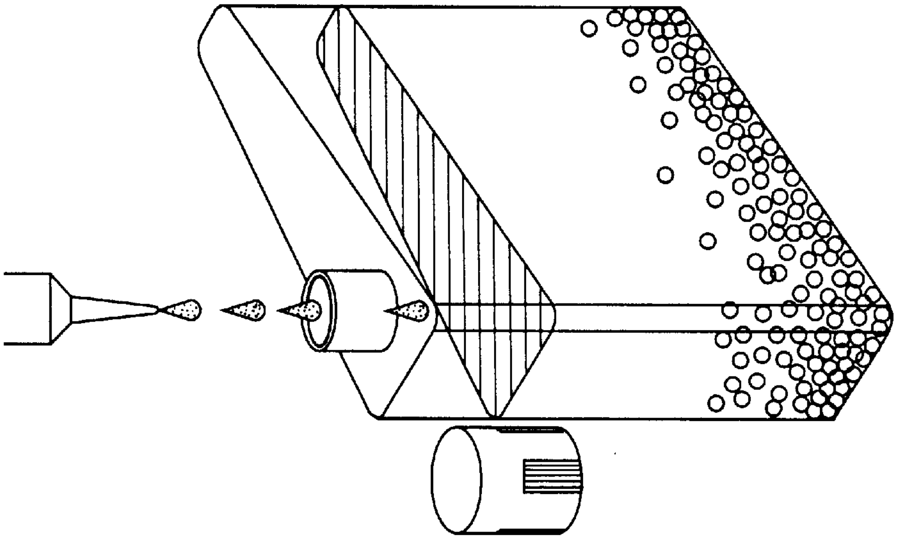
Figure 3A:
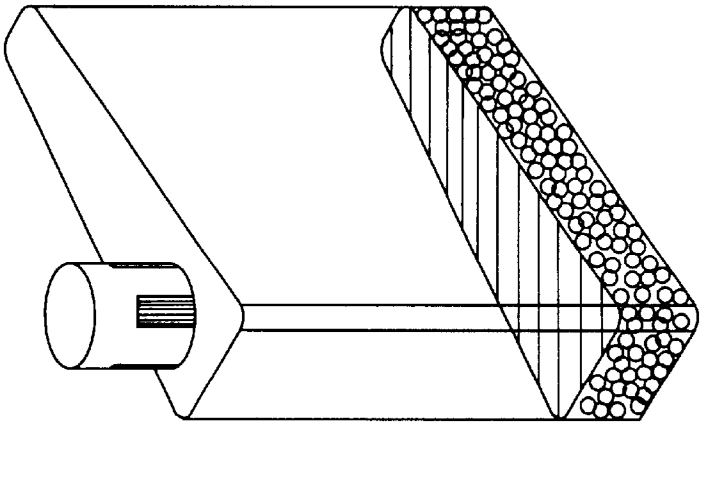

FIG. 3 shows the preparation of a liquid from a solid and a liquid. In representation A the solid is located in the vessel closed by the desiccant stopper. After opening the vessel (removal of the desiccant stopper) representation B shows the addition of liquid to the solid. After closing the vessel with the aforementioned cap or with a new cap, the solid is mixed in representation C with the liquid phase by shaking.

LIST OF REFERENCE NUMBERS

(1): Desiccant stopper
(2): Wall of the desiccant stopper
(3): Thread of the desiccant stopper
(4): Desiccant chamber
(5): Hollow plug of the desiccant stopper
(6): Separating element
(7): Flanging

EXAMPLES

Example 1

Preparation of liquid reagents by dissolving the solid reagents with water.

Barrier effect of a separating element in the form of cardboard and inertness of the drying chamber towards chemicals.

Preparation of the Liquid Reagent

Systems were tested for the preparation of liquids from solid reaction mixtures for the clinical-chemical determination of aspartate aminotransferase (GOT) and alanine aminotransferase (GPT) by reaction with nicotinamide adenine dinucleotide (NADH).

In order to prepare the ready-to-use reagent, solids were partially dissolved by filling the vessels with water and, after screwing on the desiccant screw cap and shaking, finally dissolved in the precalculated amount of water. The reagent solution which is formed for the determination of GOT then had the following composition:

| | | |
|---|---|---|
| Tris | 27.8 | mmol/l |
| Tris · HCl | 58.4 | mmol/l |
| L-aspartate | 254 | mmol/l |
| α-ketoglutarate | 12.7 | mmol/l |
| NADH | 0.19 | mmol/l |
| 2-chloroacetamide | 10.7 | mmol/l |
| MDH | 1200 | U/l |
| LDH | 4390 | U/l |
| polyvinylpyrrolidone ca. | 0.1% | by weight |

The reagent solution for the determination of GPT had the following composition:

| | | |
|---|---|---|
| Tris | 15.9 | mmol/l |
| Tris · HCl | 89.6 | mmol/l |
| L-alanine | 530 | mmol/l |
| α-ketoglutarate | 15.9 | mmol/l |
| NADH | 0.19 | mmol/l |
| 2-chloroacetamide | 10.7 | mmol/l |
| LDH | 8900 | U/l |
| polyvinylpyrrolidone ca. | 0.1% | by weight |

Examination of the Barrier Effect

The vessels were stored upside down for 24 hours which far exceeds the stress in normal usage.

In order to test the barrier effect towards liquids, the screw caps were subsequently unscrewed and the cardboard separating elements (cardboard UD2 from the Laakmann GmbH Company) were removed in order to inspect the desiccant. In all cases the desiccant was still dry i.e. the barrier effect was present in all cases.

Examination of the chemical inertness of the desiccant chamber.

The chemical function was evaluated using 2 test criteria:

1. Control of function by determining the recovery of a defined amount of GOT or GPT in a control sample (w [%]) in relation to the reference value which was set at 100%.
2. Content of active substance (NADH content) was determined photometrically by the absorbance at 340 nm.

The following reaction sequences proceed in the case of 1.:

GOT:

$$\text{L-aspartate} + \alpha\text{-ketoglutarate} \xrightleftharpoons{\text{GOT}} \text{oxaloacetate} + \text{L-glutamate} \quad \text{(I)}$$

$$\text{oxaloacetate} + \text{NADH} + \text{H}' \xrightleftharpoons{\text{MDH}} \text{L-malate} + \text{NAD}^+ \quad \text{(II)}$$

GPT:

$$\text{L-alanine} + \alpha\text{-ketoglutarate} \xrightleftharpoons{\text{GPT}} \text{pyruvate} + \text{L-glutamate} \quad \text{(I)}$$

$$\text{pyruvate} + \text{NADH} + \text{H}' \xrightleftharpoons{\text{LDH}} \text{L-lactate} + \text{NAD}^+ \quad \text{(II)}$$

(II): Reaction II is the so-called indicator reaction for photometric detection.

The experimental results are shown in the following Table:

| | Reference | 8 h/ upside down | 16 h/ upside down | 24 h/ upside down | rotate |
|---|---|---|---|---|---|
| GOT reagent | | | | | |
| w [%] | 100.00 | 99.87 | 99.87 | 99.41 | 99.74 |
| NADH absorbance | 1.370 | 1.392 | 1.397 | 1.430 | 1.373 |
| GPT reagent | | | | | |
| w [%] | 100.00 | 99.92 | 99.44 | 99.12 | 99.76 |
| NADH absorbance | 1.392 | 1.400 | 1.412 | 1.406 | 1.390 |

The measured values show that the function of the reagent and the content of active substance is only negligibly influenced by the presence of the desiccant stopper even under extreme stresses.

Example 2

Maintenance of Dryness During Storage

In each case 2 batches of solid reagent mixtures for the clinical-chemical determination of aspartate aminotransferase (GOT) and alanine aminotransferase (GPT) are examined.

The solid which can be used to prepare a reagent liquid for the determination of GPT contained in 100 g granulate:

| | | |
|---|---|---|
| Tris | 2.72 | g |
| Tris · HCl | 20.06 | g |
| L-alanine | 67.07 | g |
| α-ketoglutarate | 5.09 | g |
| NADH | 1.34 | g |
| 2-chloroacetamide | 1.42 | g |
| LDH | ca. 0.34 | g |
| polyvinylpyrrolidone | ca. 1.93 | g |

5.7 g of this mixture was stored in a system made of poylethylene with a wall thickness of ca. 1 mm, in which case 1.4 g desiccant (D) in the form of a molecular sieve (type 511 from the Grace GmbH Company) was used.

An analogous mixture for the determination of GOT contained per 100 g granulate:

| | | |
|---|---|---|
| Tris | 5.31 | g |
| Tris · HCl | 14.48 | g |
| L-aspartate Na salt | 70.31 | g |
| α-ketoglutarate | 4.51 | g |
| NADH | 1.48 | g |
| 2-chloroacetamide | 1.57 | g |
| MDH | ca. 0.22 | g |
| LDH | ca. 0.19 | g |
| polyvinylpyrrolidone | ca. 1.97 | g |

In this experiment 7.0 g of the mixture was stored using 1.4 g of the aforementioned molecular sieve as the desiccant.

In order to determine the ability of the system to function, a system with desiccant screw cap was compared in each case with vessels without a desiccant screw cap which were otherwise of equal quality.

The test criteria were

1. Water content in the filling material; determined with the Karl-Fischer method.
2. Content of active substance (NADH content); determined photometrically by the absorbance at 340 nm.

| | Water content % by weight | | Absorbance 340 nm | |
|---|---|---|---|---|
| Stress period | with D | without D | with D | without D |
| GOT | | | | |
| 0 weeks | 8.18% | 8.18% | 1.513 | 1.513 |
| 3 weeks | 7.69% | 8.46% | 1.564 | 1.069 |
| 6 weeks | 7.80% | 9.20% | 1.493 | 0.705 |
| GPT | | | | |
| 0 weeks | 0.79% | 0.79% | 1.506 | 1.506 |
| 3 weeks | 0.67% | 1.04% | 1.542 | 1.321 |
| 6 weeks | 0.89% | 1.23% | 1.486 | 0.781 |

The "GOT" example in addition shows that only the mobile moisture that is critical for stability is selectively removed and the immobile portion of the crystal water which is uncritical for stability remains uninfluenced.

Example 3

Redrying of a Granulate Containing Water Due to the Manufacturing Process.

5.7 g granulate with an initial water content of 0.59% by weight (determined with the Karl-Fischer method) was dispensed into a system for the preparation of liquids and this was closed with the accompanying desiccant screw cap. The composition of the granulate corresponded to the mixture for the determination of GPT mentioned in example 2. The cardboard Duplex 1 UD2 from the Laakmann Company was used as the separating element. 1.4 g molecular sieve was used as the desiccant.

The system was kept at room temperature during the redrying phase and the water content was determined periodically with the Karl-Fischer method.

Figure 4:
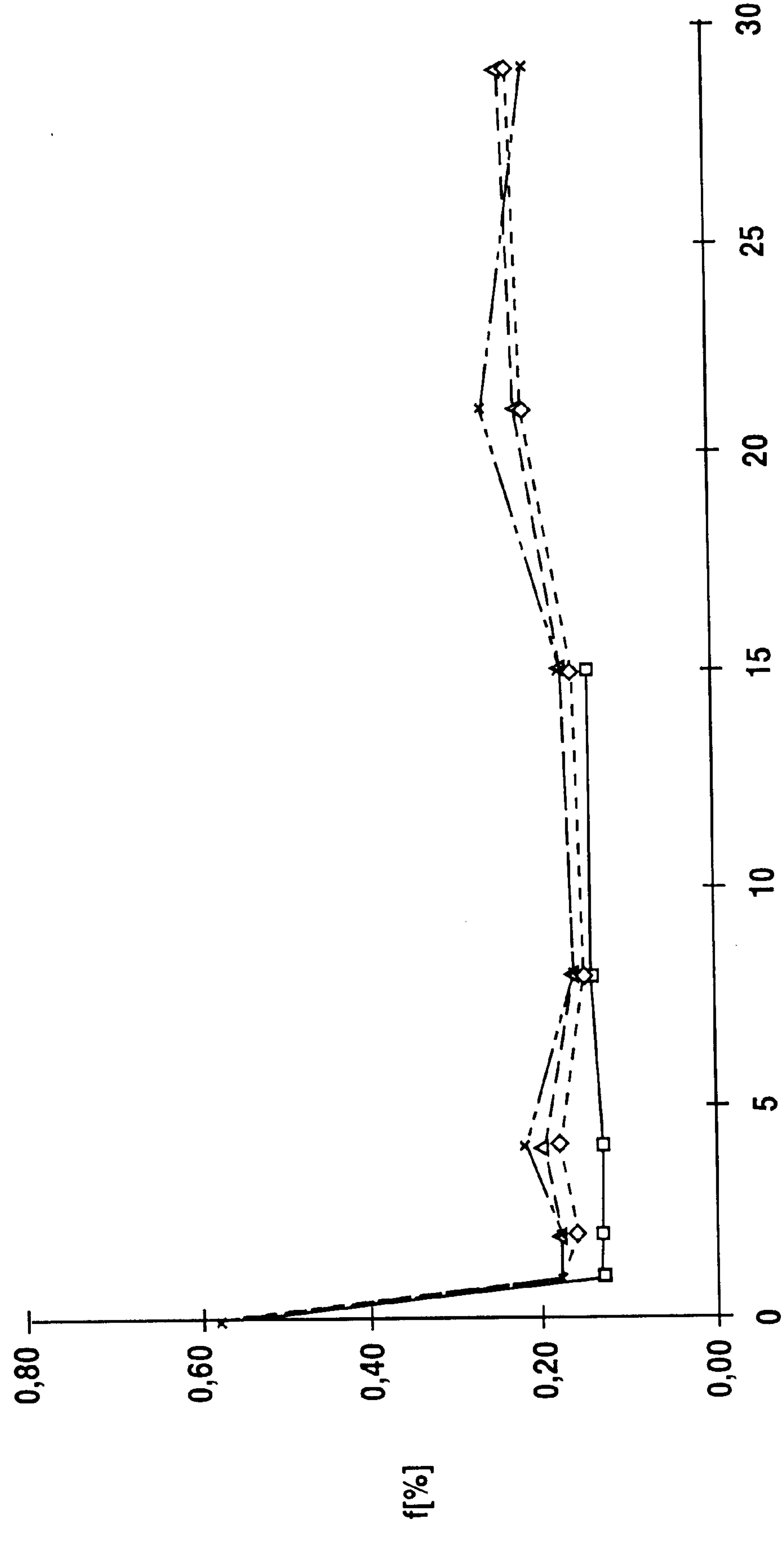
FIG. 4: Moisture content of a solid when stored in various systems according to the invention.

FIG. 4 shows the dependence of the water content (f) on the storage time (t) in days in the system. Various combinations of vessel sizes are shown in the figure:

□ml vessel volume; 2 ml desiccant

◇ ml vessel volume; 2 ml desiccant

Δml vessel volume; 2 ml desiccant x: ml vessel volume; 4 ml desiccant

After one day the granulate was redried to a water content of less than 0.2% by weight in all bottles.

What is claimed:

1. An apparatus for the preparation of a liquid from at least one solid and at least one liquid phase, comprising:

a vessel which defines a compartment which contains said at least one solid, said compartment having a volume which is sufficient to receive said at least one solid and said at least one liquid phase;

a desiccant article which defines a desiccant chamber which contains a desiccant; and a separating element which is permeable to water vapor and which separates said desiccant chamber from said compartment, such that said desiccant can exchange water vapor with said compartment and direct contact of liquid or solid contents in said compartment with said desiccant is substantially prevented, wherein said separating element is made of cardboard and has a surface tension for wetting which is smaller than 70 mN/m.

2. An apparatus as claimed in claim 1, wherein said desiccant article is selectively engageable with said vessel so as to close said compartment.

3. An apparatus as claimed in claim 1, wherein said vessel is composed of a material which is at least partially permeable to water vapor.

4. An apparatus as claimed in claim 1, wherein said separating element has a surface tension for wetting of from 25 to 65 mN/m.

5. An apparatus as claimed in claim 1, wherein said separating element has a critical surface tension for wetting of from 30 to 40 mN/m.

6. The apparatus of claim 1, wherein said desiccant chamber is closed to the outside by a wall.

7. The apparatus of claim 6, wherein said wall is composed of a plastic, a metal or a cardboard material.

8. A process for the production of a liquid, comprising:

a) storing a solid in a compartment defined by a vessel, said vessel being separated from a desiccant chamber by a separating element which is permeable to water vapor, said desiccant chamber containing a desiccant, such that said desiccant can exchange water vapor with said compartment and direct contact of liquid or solid contents in said compartment with said desiccant is substantially prevent;

b) opening said vessel;

c) adding liquid phase to said solid in said compartment;

d) closing said vessel; and e) mixing said solid and said liquid phase so that a solution, suspension or emulsion is formed.

9. A process as claimed in claim 8, comprising closing said vessel with said desiccant chamber before as well as after said adding of said liquid phase.

10. A process as claimed in claim 8, wherein said solid is placed in said compartment in an atmosphere containing water vapor.

11. A process as claimed in claim 8, wherein said adding of said liquid phase is carried out by a filling device.

12. A process as claimed in claim 8, wherein said solution, suspension or emulsion is withdrawn from said compartment by a withdrawing device.

13. A process as claimed in claim 8, wherein said liquid phase is prepared by a mixing device.

14. A process as claimed in claim 8, wherein said storing of said solid in said vessel serves to dry or maintain dryness of said solid.

15. A process as claimed in claim 14, wherein said storing of said solid in said vessel serves to dry and maintain dryness of said solid.

16. A process as claimed in claim 8, wherein said opening of said vessel in step b) is achieved by piercing with a cannula.

17. A process according to claim 8, wherein said mixing of said solid and said liquid phase produces a reagent solution.

18. The process of claim 8, wherein said desiccant chamber is closed to the outside by a wall.

19. The process of claim 18, wherein said wall is composed of a plastic, a metal or a cardboard material.

20. A process for the production of a liquid, comprising:

a) storing a solid in a compartment defined by a vessel, said vessel being separated from a desiccant chamber by a separating element which is permeable to water vapor, said desiccant chamber containing a desiccant, such that said desiccant can exchange water vapor with said compartment and direct contact of liquid or solid contents in said compartment with said desiccant is substantially prevented;

b) opening said vessel;

c) adding liquid phase to said solid in said compartment; and d) mixing said solid and said liquid phase in an opened vessel so that a solution, suspension or emulsion is formed.

21. A process according to claim 20, wherein said mixing of said solid and said liquid phase produces a reagent solution.

22. The process of claim 20, wherein said desiccant chamber is closed to the outside by a wall.

23. The process of claim 22, wherein said wall is composed of a plastic, a metal or a cardboard material.

* * * * *